US00PP20729P3

(12) United States Plant Patent
Crisosto

(10) Patent No.: US PP20,729 P3
(45) Date of Patent: Feb. 9, 2010

(54) PERSIMMON TREE NAMED 'NUEVO ROJO BRILLANTE'

(50) Latin Name: *Diospyros kaki L.*
Varietal Denomination: Nuevo Rojo Brillante

(76) Inventor: Carlos H. Crisosto, 9240 S. Riverbend Ave., Parlier, CA (US) 93648

( * ) Notice: Subject to any disclaimer, the term of this patent is extended or adjusted under 35 U.S.C. 154(b) by 0 days.

(21) Appl. No.: 12/070,896

(22) Filed: Feb. 20, 2008

(65) Prior Publication Data

US 2009/0210973 P1 Aug. 20, 2009

(51) Int. Cl.
*A01H 5/00* (2006.01)

(52) U.S. Cl. ..... Plt./156

(58) Field of Classification Search ..... Plt./156
See application file for complete search history.

(56) References Cited

OTHER PUBLICATIONS

Badenes et al., (2002), "Generic Diversity of Persimmon Accession Introduced and Surveyed in Spain," Options Mediterraneennes Serie A 51:71-73.*

Llacer et al. (2002), "Persimmon Production and Market," Options Mediterraneennes Serie A 51:9-21.*

Badenes et al., (2002). "Genetic Diversity of Persimmon Accessions Introduced and Surveyed in Spain," *Options Méditerrranéennes Série A* 51:71-73.

Giordani, E. (2002), "Varietal Assortment of Persimmon in the Countries of the Mediterranean Area and Genetic Improvement," *Options Méditerranéennes Série A* 51:23-37.

Llácer et al. (2002), "Persimmon Production and Market," *Options Méditerranéennes Série A* 51:9-21.

* cited by examiner

*Primary Examiner*—June Hwu
(74) *Attorney, Agent, or Firm*—Morrison & Foerster LLP

(57) ABSTRACT

The persimmon tree of the present invention is characterized by producing a large highly colored fruit. The new variety most closely resembles the 'Rojo Brillante' persimmon tree, but it is distinguished in a number of respects including that 'Nuevo Rojo Brillante' retains a higher cheek firmness after astringency removal than 'Rojo Brillante.' Also, the color after astringency removal of 'Nuevo Rojo Brillante' is more yellow-orange than that of 'Rojo Brillante.' 'Nuevo Rojo Brillante' is a pollination-variant astringent cultivar (PVA).

1 Drawing Sheet

Botanical/commercial classification: *Diospyros kaki* L.
Variety denomination: 'Nuevo Rojo Brillante'.

BACKGROUND OF THE INVENTION

Commercial varieties of fruit trees may be distinguished from one another by a multiplicity of characteristics. Furthermore, there are many varieties of certain fruit trees while other types of fruit trees have only a few commercially recognized varieties. For example, peach trees have a plethora of recognized commercial varieties while persimmon trees have very few. Thus, in the case of persimmon trees, there are considerably fewer varieties from which to choose, of course both in the trees and the fruit there from. This makes new varieties of persimmon trees potentially of significantly more importance than is the case with peach trees. When this fact is coupled with all of the distinguishing characteristics, such as ripening date, size, coloration, flavor and the like, the commercial potential of such varieties may be significant.

The persimmon tree of the present invention appears to be a promising candidate in these regards, as will hereinafter be set forth in greater detail.

BRIEF SUMMARY OF THE INVENTION

The present invention relates to a new and distinct variety of persimmon tree, which will hereinafter be denominated as 'Nuevo Rojo Brillante', and more particularly, to a persimmon tree which produces fruit which are mature for commercial harvesting and shipment approximately the second-fourth week of November near Kingsburg in the southern San Joaquin Valley of California.

DETAILED DESCRIPTION OF THE INVENTION

Figure 1:
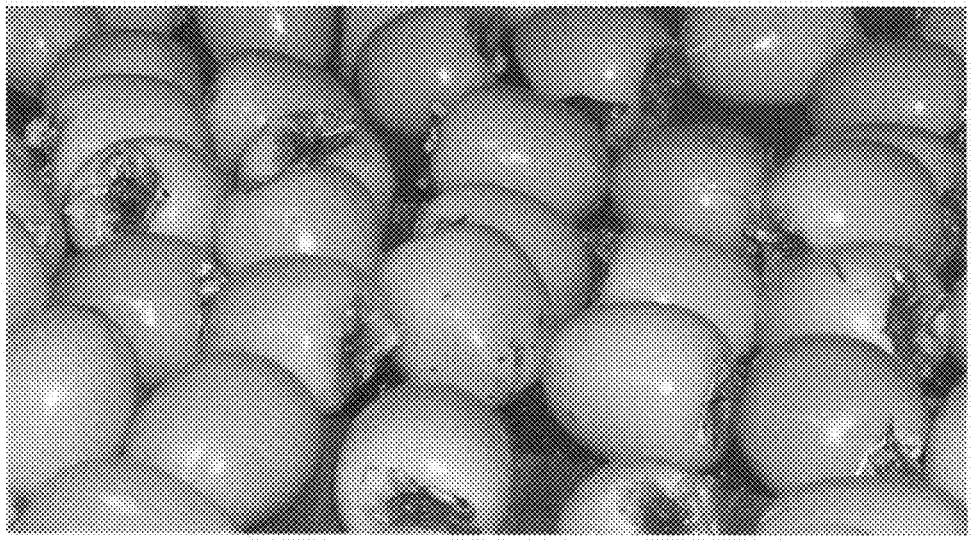
FIG. 1: a color photograph of 'Nuevo Rojo Brillante:' (A) before astringency removal treatment; and (B) after astringency removal treatment.
Figure 1:
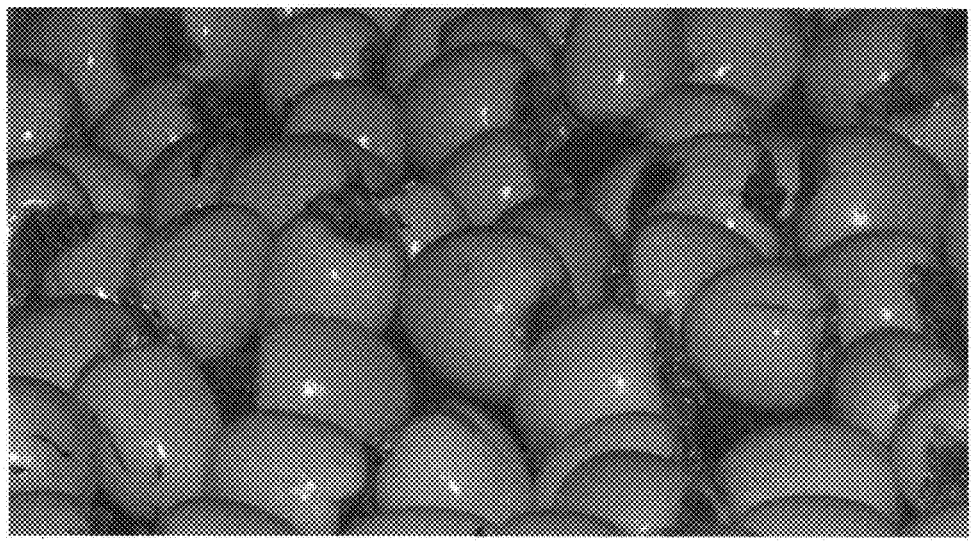

'Rojo Brillante' (not patented) was selected by local Spanish growers in the 1960s among many wild persimmons growing in the Ribera del Júcar, south of Valencia. In March of 2005, six accession cuttings of the 'Rojo Brillante' cultivar were imported from Spain, grafted on *Diospyros lotus* rootstocks, and placed under quarantine in Kingsburg, Calif. After the quarantine period, the trees were asexually reproduced in Kingsburg, Calif. by grafting bud wood of the variety on to *Diospyros kaki* rootstocks. The 'Rojo Brillante' cultivar was selected based on bloom time. From the six accession cuttings of 'Rojo Brillante' several persimmon trees were produced by whip grafting, and their horticultural performance has been evaluated over the years. Three trees were selected that originated from one cutting that expressed different important horticulture traits compared to trees originating from the other five cuttings. The three selected trees were named 'Nuevo Rojo Brillante.' 'Nuevo Rojo Brillante' was asexually reproduced by whip graft in Kingsburg, Calif. Botanical trait and quality trait measurements were carried out on the 'Nuevo Rojo Brillante' tree. As of early 2008, the 'Nuevo Rojo Brillante' tree was approximately three years old.

One of the different horticultural traits observed in 'Nuevo Rojo Brillante,' was that leafing and blooming occurs 4–7 days later than in 'Rojo Brillante'. Delayed leafing and blooming may help to avoid crop damage resulting from spring frost. In some seasons, this delay in blooming may also affect harvesting date, but this effect has not yet been observed. The 'Nuevo Rojo Brillante' cultivar is in the pollination-variant astringent (PVA) group, thus fruits are astringent at harvest with a full orange-yellow flesh. 'Nuevo Rojo Brillante' fruit is ripe for commercial harvesting and shipment during the second to fourth week of November in the southern San Joaquin Valley of California.

Another of the different horticultural traits observed in 'Nuevo Rojo Brillante' was firmness retention. Firmness retention is a very important trait for the successful marketing of healthy fruit, such as 'Nuevo Rojo Brillante,' under current fruit handling conditions. It is worth noting that improved firmness has been reported in other species such as peaches, plums, and nectarines. Various fruit breeding programs have selected for mutations of enzymes related to softening, such as endo and exo PG, to produce very successful improved firmness cultivars. Several new cultivars have become commercially available based on the firmness retention characteristic. Experience with fruit behavior during postharvest handling, transportation, and marketing has shown that a 3 to 5 pound difference in fruit firmness allows for the extension of storage and shelf life. The 'Nuevo Rojo Brillante' tree was selected for based on fruit firmness that was approximately 3 to 5 pounds greater than 'Rojo Brillante,' which allowed for an extension of storage and shelf life over 'Rojo Brillante.'

Fruit from 'Nuevo Rojo Brillante' trees tolerated postharvest astringency removal treatment much better than fruit from 'Rojo Brillante' trees. The astringency removal treatment consisted of exposing persimmon fruit to high carbon dioxide levels (95%) for 12 hours at room temperature (20° C.). This treatment is essential to allow the 'Nuevo Rojo Brillante' cultivar to be freshly consumed.

Firmness evolution (softening) of 'Nuevo Rojo Brillante' fruit was followed after the astringency removal treatment during cold and warm storage. The 'Nuevo Rojo Brillante' fruit remained commercially firmer than fruit from 'Rojo Brillante' during astringency removal treatment and postharvest handling (storage and simulated shelve display). Cheek fruit firmness of ripe 'Nuevo Rojo Brillante' ranges from 7.7 to 10.7 pounds, while the cheek fruit firmness of 'Rojo Brillante' ranges from 5.6 to 6.0 pounds.

The average color of 'Rojo Brillante' and 'Nuevo Rojo Brillante' was objectively expressed as hue angle (h*). The hue angle is expressed in degrees and is a measure of color, for example from 0° to 90° spanning from red to orange to yellow. The hue angle is based on the Commission Internationale de l'Eclairage CIELAB (L*a*b*) scale and was measured with a Minolta Chromameter CR-200 (Minolta Corp., Ramsey, N.J.). Both 'Rojo Brillante' and 'Nuevo Rojo Brillante' were harvested based on visual skin color (yellow to orange-yellow). The hue angle in these two groups ranged from 65.85° to 74.80° with an average of 68.97°.

After astringency removal 'Nuevo Rojo Brillante' fruit had hue angle values that ranged from 62.50° to 70.00° with an average of 63.17° (yellow-orange). However, 'Rojo Brillante' fruit had hue angle values that ranged from 43.00° to 57.30° with an average of 52.87° (orange), after astringency removal.

Table 1 depicts the trait differences between 'Nuevo Rojo Brillante' and 'Rojo Brillante.'

TABLE 1

| Trait | 'Nuevo Rojo Brillante' | 'Rojo Brillante' |
|---|---|---|
| Cheek Fruit Firmness | 7.7 to 10.7 pounds | 5.6 to 6.0 pounds |
| Hue Angle After Astringency Removal | 62.50° to 70.00° | 43.00° to 57.30° |

The persimmon tree of the instant variety were also readily distinguishable from the 'Hachiya' (not patented) persimmon variety in numerous respects, including that 'Nuevo Rojo Brillante' produced fruit which was ripe for commercial harvesting and shipment 10–20 days later that the fruit of the 'Hachiya' persimmon trees. 'Nuevo Rojo Brillante' fruit matures at the same time as 'Fuyu' persimmon. 'Nuevo Rojo Brillante' fruit is larger and has a brighter orange color at harvest than 'Hachiya.' 'Hachiya' blossom color end is orange or reddish color equal to or darker than Munsell color 6.7 YR 5.93/12.7, and has a cheek firmness of about 9.0 pounds.

DETAILED BOTANICAL DESCRIPTION

Referring more specifically to the pomological details of this new and distinct variety of persimmon tree, the following has been observed under the ecological conditions prevailing in the orchard of origin located near Kingsburg in the southern San Joaquin Valley of California.

Tree:

*Generally.*—'Nuevo Rojo Brillante' tree is large to medium in size with high vigor and trained to grow on an open vase.

*Size.*—Height, ten to twelve feet.

*Size.*—Width, ten to twelve feet when trained to grow in an open vase.

*Vigor.*—High.

*Productivity.*—Very high.

*Regularity of bearing.*—'Nuevo Rojo Brillante' is compatible with *Diospyros lotus* and *D. virginiana,* and no alternative bearing habits have been observed in Spain which has similar climatic conditions to those in the southern San Joaquin Valley of California.

*'Nuevo Rojo Brillante' hardiness zone.*—USDA zone 8–10; ideally California (9–10).

Trunk:

*Size.*—Medium, 40 cm (15.7 inches) to 60 cm (23.6 inches) in circumference at a point 50 cm (19.9 inches) above ground level.

*Bark color.*—Slightly light grayish tan (h*=59.1°).

*Surface texture.*—Moderately rough.

*Bark lenticel numbers.*—Moderate numbers.

*Bark lenticels size.*—Small, 5.5 cm (2.2 inches) in length.

*Bark lenticel color.*—Light ash (h*=66.4°).

Branches:

*Size.*—Medium, 25 cm (9.8 inches) to 27 cm (10.6 inches) in circumference at a point 40 cm (15.7 inches) above crotch.

*Branch color.*—Light grayish tan (h*=53.3°).

*Surface texture.*—Slightly rough.

*Angle of branches.*—43 degrees at a point approximately 36 cm (14.2 inches) above crotch.

*Branch lenticels numbers.*—Moderate.

*Branch lenticels size.*—*Small,* 3.6 cm (1.4 inches) to 4.8 cm (1.9 inches) in length.

*Branch lenticels color.*—Lighter grayish tan with a red spot (h*=54.3°).

Leaves:

*Size.*—Generally — Medium to large, pinnately veined.

*Average length.*—130 mm (5.12 inches) to 160 mm (6.30 inches).

*Average width.*—80 mm (3.15 inches) to 90 mm (3.54 inches).

*Form.*—Ovate. Leaf tip is broadly acuminate.

*Foliage upper surface color.*—Bright glossy green (h*=128.5°).

*Foliage lower surface color.*—Pale green (h*=123.7°).

*Petiole.*—Length — 10 mm (0.39 inches) to 15 mm (0.59 inches).

*Petiole.*—Thickness — 2.5 mm (0.098 inches).

*Petiole color.*—Yellowish green (97.8°).

*Glands.*—None.

*Stipule length.*—Average 3.8 mm (0.15 inches).

*Stipules shape.*—Globular.

Flowers:

*Flower buds.*—Only female (pistillated) flowers very abundant with high set and low fruit drop.

*Generally.*—Flower are dioecious. Flowers are also hardy in typical climatic conditions in the southern San Joaquin Valley of California. Flower buds are covered by large calyx.

*Size.*—Length — 12 mm (0.47 inches) to 16 mm (0.63 inches).

*Size.*—Width — 7.3 mm (0.29 inches).

*Surface texture.*—Smooth, glabrous.

*Shape.*—Winged.

*Date of bloom.*—Less than 10% by April 15. and 100% by mid May (mid season bloom).

*Calyx.*—Size — Large, 16 mm (0.63 inches) to 19 mm (0.75 inches).

*Flowers.*—Size. — Generally — Small to medium, 4.5 mm (0.177 inches) to 8 mm (0.315 inches).

*Opened flower color.*—Light green-yellow (h*=not available).

*Petals.*—Number — Four (4).

*Petals.*—Form — Broadly ovate.

*Petals.*—Size — Length — Average 7 mm (0.276 inches) to 11 mm (0.433 inches).

*Petals.*—Size — Width — 6 mm (0.236 inches) to 8 mm (0.315 inches).

*Flower pedicels.*—Medium.

*Flower pedicels.*—Length — 1 mm (0.433 inches) to 14 mm (0.551 inches).

*Flower pedicels.*—Thickness — 4 mm (0.157 inches).

*Surface texture.*—Glabrous.

*Calyx.*—Surface Texture — Glabrous.

*Sepals.*—Number — Four (4).

*Sepals.*—Size — Large.

*Sepals.*—Length — 20 mm (0.787 inches).

*Sepals.*—Width — 18 mm (0.709 inches).

*Sepals.*—Surface Texture — Glabrous.

*Sepals.*—Form — Broadly ovate.

Fruit:

'Nuevo Rojo Brillante' is in the pollination-variant astringent (PVA) group with a high parthenocarpic productivity. Glossy orange fruits (h*=68.97°) are astringent at harvest with very attractive bright red orange skin color (h*=63.17°); yellow-orange flesh without brown spots at harvest time. Fruits are edible with an excellent flavour only after submitted to an astringency removal treatment in which they turn bright red orange. 'Nuevo Rojo Brillante' matures for commercial harvesting and shipment approximately the third week of November near Kingsburg, in the southern San Joaquin Valley of California. The time from removal of astringency, which is done right after harvest, to eating is temperature depending. Treated 'Nuevo Rojo Brillante' can be stored for approximately 7 to 9 weeks at 50° F. and 90% relative humidity (RH), and can be 'ready to eat' within 1 to 2 days after astringency removal.

*Size.*—Generally uniform and large for oriental persimmon, averaging 250–300 grams per fruit with an average diameter of at least 61 mm.

*Calyx.*—Slightly depressed attachment to fruit, has a horizontal attitude in relation to the fruit, and size is larger than fruit diameter.

*Form.*—Very broad ovate shape.

*Apex.*—Obtuse shape, weak to moderate grooving, and cracking is absent.

*Skin.*—Thickness. — Average for persimmons.

*Texture.*—Glabrous.

*Tenacity.*—Adheres tightly to flesh.

*Tendency to crack.*—None observed.

*Fruit color.*—Overall color at maturity covered whole fruit with a fully orange color (h*=68.97°). On fruit after ripening the orange color turns bright red orange (h*=63.17°).

*Flesh color.*—Uniform yellow orange throughout on the fruit.

*Seeds.*—When pollinated will produce seeds and brown areas around the seeds.

*Flavor.*—Astringent on mature fruit, very sweet after astringency removal.

*Eating quality.*—Astringent similar to 'Rojo Brillante' and 'Hachiya,' excellent after astringency has been removed.

*Plant/fruit disease and pest resistance/susceptibility.*—None observed.

*Use.*—Drying and fresh market only after special ripening (astringency removal treatment).

Although the new variety of persimmon tree possesses the described characteristics noted above as a result of the growing conditions prevailing near Kingsburg, Calif. in the southern San Joaquin Valley of California, it is to be understood that variations of the usual magnitude and characteristics incident to changes in growing conditions, irrigation, fertilization, pruning, pest control, climatic variations and the like, are to be expected.

What is claimed is:

1. A novel and distinct variety of persimmon tree herein denominated 'Nuevo Rojo Brillante' having the characteristics described and illustrated herein.

* * * * *

A

B